(12) United States Patent
Slany et al.

(10) Patent No.: US 6,723,882 B2
(45) Date of Patent: Apr. 20, 2004

(54) PREPARATION OF DIALKYL KETONES

(75) Inventors: Michael Slany, Kirchheim (DE); Martin Schäfer, Grünstadt (DE); Michael Röper, Wachenheim (DE)

(73) Assignee: BASF Aktiengesellschaft, Ludwigschafen (DE)

( * ) Notice: Subject to any disclaimer, the term of this patent is extended or adjusted under 35 U.S.C. 154(b) by 0 days.

(21) Appl. No.: 10/197,447

(22) Filed: Jul. 18, 2002

(65) Prior Publication Data

US 2003/0069450 A1 Apr. 10, 2003

(30) Foreign Application Priority Data

Jul. 28, 2001 (DE) .......................................... 101 37 079

(51) Int. Cl.$^7$ .............................................. C07C 45/49
(52) U.S. Cl. ...................... 568/387; 568/395; 568/401; 568/404
(58) Field of Search ................................ 568/387, 395, 568/401, 404

(56) References Cited

U.S. PATENT DOCUMENTS

| 3,829,499 A | 8/1974 | Nozaki |
| 4,602,116 A | 7/1986 | Cooper |
| 5,846,453 A | 12/1998 | Mohr |

FOREIGN PATENT DOCUMENTS

| DE | 1 793320 | 3/1971 |
| DE | 2 061798 | 6/1971 |
| DE | 37 27704 | 3/1989 |
| EP | 274 795 | 7/1988 |
| EP | 282 142 | 9/1988 |
| EP | 322 811 | 7/1989 |
| EP | 386 833 | 9/1990 |
| EP | 441 446 | 8/1991 |
| EP | 495 547 | 7/1992 |
| EP | 495 548 | 7/1992 |
| EP | 577 204 | 1/1994 |
| EP | 577 205 | 1/1994 |
| GB | 2 202 165 | 9/1988 |
| GB | 2 208 480 | 4/1989 |
| WO | 94/18154 | 8/1994 |
| WO | 96/19434 | 6/1996 |
| WO | 98/42717 | 10/1998 |
| WO | 98/45040 | 10/1998 |

OTHER PUBLICATIONS

Derwent 84–079864/13.
Ullmann's Enc.Inc.Chem.6thEd, Siegel et al.

*Primary Examiner*—James O. Wilson
*Assistant Examiner*—Sikarl A. Witherspoon
(74) *Attorney, Agent, or Firm*—Keil & Weinkauf

(57) ABSTRACT

Dialkyl ketones are prepared by reductive carbonylation of α-olefins by means of carbon monoxide and hydrogen in the presence of a catalyst system comprising (a) palladium or a palladium compound;
(b) a phosphine;
(c) a protic acid having a $pK_a$ of $\leq 4.5$, measured in aqueous solution at 25° C.; and
(d) a solubilizable carboxamide.

10 Claims, No Drawings

PREPARATION OF DIALKYL KETONES

The present invention relates to a process for preparing dialkyl ketones by reductive carbonylation of α-olefins by means of carbon monoxide and hydrogen in the presence of a catalyst system.

Dialkyl ketones are important solvents and intermediates for organic syntheses. Thus, in particular, 3-pentanone (diethyl ketone) is an excellent solvent for paints. Furthermore, 3-pentanone is used in numerous syntheses, for example the preparation of trimethylphenol and of vitamin E.

Dialkyl ketones are obtainable via a wide variety of synthetic routes, for instance by ketonization of carboxylic acids or aldehydes or by oxidation of secondary alcohols, of olefins or of alkanes. Disadvantages of these synthetic routes are the use of expensive intermediates (carboxylic acids, aldehydes, secondary alcohols, olefins having a central double bond) and often unsatisfactory selectivities and yields in the oxidation of olefins and alkanes.

A further synthetic route is reductive carbonylation of α-olefins (olefins having a terminal double bond) in the presence of hydrogen, water or compounds having a reducing action, e.g. alcohols (cf. Ullmann's Encyclopedia of Industrial Chemistry, 6$^{th}$ edition, 2000 electronic release, Chapter "KETONES—Dialkyl Ketones"). A disadvantage of the use of water as hydrogen source is the additional consumption of stoichiometric amounts of carbon monoxide for binding the oxygen. A disadvantage of the use of compounds having a reducing action is the associated coproduction of the corresponding oxidation products.

In the reductive carbonylation of α-olefins in the presence of carbon monoxide and hydrogen to form the corresponding dialkyl ketones, use is usually made of metals of groups 8 to 10 of the Periodic Table. DE-A 2 061 798 discloses carbonylation in the presence of cobalt carbonyl complexes and ammonia, an amine or a nitrile at a pressure of preferably from 4.5 to 140 atmospheres (from 0.45 to 14 MPa abs). U.S. Pat. No. 4,602,116 describes carbonylation in the presence of triruthenium dodecacarbonyl at a pressure of preferably from 1000 to 2500 psig (from 7 to 17.3 MPa abs). GB-A 2 208 480 discloses carbonylation in the presence of a ruthenium compound, a protic acid and a water-soluble solvent at a pressure of preferably from 5 to 7.5 MPa abs. DE-A 1 793 320 teaches carbonylation in the presence of a rhodium-containing catalyst at a pressure of from 200 to 300 atm (from 20 to 30 MPa abs). GB-A 2 202 165 describes carbonylation in the presence of a platinum(II) compound, a diphosphine and a protic acid at a pressure of preferably from 2 to 7.5 MPa abs.

Disadvantages of the abovementioned processes are the unsatisfactory stability of the catalyst systems and the high pressure necessary in carrying out the carbonylation.

EP-A 0 322 811 teaches the reductive carbonylation of α-olefins to form the corresponding dialkyl ketones in the presence of a catalyst system comprising a rhodium complex, a phosphine and a para-substituted benzoic acid having an electron-withdrawing substituent in the para position. Disadvantages of the abovementioned process are the unsatisfactory selectivity (coproduction of aldehyde and ketone) and the (lack of) stability of the catalyst system.

SU-A 813 903 teaches the carbonylation of olefins in the presence of hydrogen to form the corresponding dialkyl ketones in the presence of palladium(II) acetate, triphenylphosphine and trifluoroacetic acid at atmospheric pressure. A selectivity of 50–98% is described for the synthesis of diethyl ketone. A disadvantage of this process is the very low activity of the catalyst system.

It is an object of the present invention to find a process for preparing dialkyl ketones which no longer has the above-described disadvantages, is based on economically attractive and readily available raw materials, avoids the formation of coproducts, utilizes a very stable, active and long-lived catalyst system and makes it possible to prepare dialkyl ketones in high yield even under mild reaction conditions.

We have found that this object is achieved by a process for preparing dialkyl ketones by reductive carbonylation of α-olefins by means of carbon monoxide and hydrogen in the presence of a catalyst system comprising (a) palladium or a palladium compound;
(b) a phosphine;
(c) a protic acid having a $pK_a$ of $\leq 4.5$, measured in aqueous solution at 25° C.; and
(d) a solubilizable carboxamide.

The presence of a solubilizable carboxamide is essential for the stability, activity and longevity of the catalyst system.

The carboxamides to be used in the process of the present invention are solubilizable in the reaction mixture and are also present in solubilized form under the reaction conditions. For the purposes of the present invention, the term "solubilized" refers to a largely homogeneous distribution of the carboxamide in the reaction mixture, which is able to stabilize the catalyst system sufficiently. In general, the carboxamide is homogeneously dissolved in the reaction mixture or at least colloidally dispersed.

The carboxamides to be used in the process of the present invention have at least one carboxamide group of the formula —CO—N< the molecule. The molar mass of the carboxamides can vary within a wide range from low molecular weight carboxamides having one carboxamide group in the molecule through to high molecular weight, polymeric carboxamides having a molecular weight of a few hundred thousand g/mol and a few hundred or a few thousand carboxamide groups in the molecule.

The chemical structure of the carboxamides to be used in the process of the present invention plays a minor role. Thus, the carboxamides can be, for example, saturated or unsaturated, aliphatic, aromatic or araliphatic compounds. Furthermore, the carboxamide can contain one or more heteroatoms such as oxygen, nitrogen, sulfur or phosphorus, for example —O—, —S—, —NH—, —NR—, —CO—, —CO—O—, —N=, —CO—N<, —SiR$_2$—, —PR— and/or —PR$_2$ and/or be substituted by one or more functional groups containing, for example, oxygen, nitrogen, sulfur and/or halogen atoms.

As carboxamides having one carboxamide group of the formula —CO—N< in the molecule, preference is given to carboxamides of the formula (II)

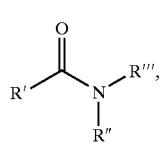

(II)

where the radicals R', R" and R'" are each, independently of one another, hydrogen;

an acyclic or cyclic alkyl radical having from 1 to 30 carbon atoms which may contain one or more heteroatoms such as oxygen, nitrogen, sulfur or phosphorus, for example —O—, —NH—, —NR—, —CO— and/or —CO—O—, and/or may bear one or more functional, aromatic or heteroaromatic groups containing, for example, oxygen, nitrogen, sulfur and/or halogen atoms, for example —OH, —CHO, —NH$_2$, —COOH, —F, —Cl, —Br and/or —CN, as substituents, for example methyl, ethyl, 1-propyl, 2-propyl (sec-propyl), 1-butyl, 2-butyl (sec-butyl), 2-methyl-1-propyl (isobutyl), 2-methyl-2-propyl (tert-butyl), 1-pentyl, 2-pentyl, 3-pentyl, 3-methyl-2-butyl, 2-methyl-2-butyl, 1-hexyl, 1-heptyl, 1-octyl, 2-ethyl-1-hexyl, 1-nonyl, 1-decyl, 1-dodecyl, 1-tetradecyl, 1-hexadecyl, 1-octadecyl, 1-eicosyl, cyclopentyl, cyclohexyl, cyclooctyl, phenylmethyl (benzyl), 2-phenyl-1-ethyl; or an aromatic radical having 1 or 2 aromatic rings and from 3 to 30 carbon atoms which may contain one or more heteroatoms, for example nitrogen, and/or may bear one or more functional or aliphatic groups containing, for example, oxygen, nitrogen, sulfur and/or halogen atoms, for example —OH, —CHO, —NH$_2$, —COOH, —F, —Cl, —Br and/or —CN, as substituents, for example phenyl, 2-methylphenyl (2-tolyl), 3-methylphenyl (3-tolyl), 4-methylphenyl (4-tolyl), 2,4-dimethylphenyl, 2,6-dimethylphenyl, 2,4,6-trimethylphenyl, 1-naphthyl, 2-naphthyl.

Particularly preferred carboxamides having one carboxamide group of the formula —CO—N< in the molecule are carboxamides (II) in which the radicals R', R" and R'" are each, independently of one another, a C$_1$–C$_{10}$-alkyl radical, for example methyl, ethyl, 1-propyl, 2-propyl (sec-propyl), 1-butyl, 2-butyl (sec-butyl), 2-methyl-1-propyl (isobutyl), 2-methyl-2-propyl (tert-butyl), 1-pentyl, 2-pentyl, 3-pentyl, 3-methyl-2-butyl, 2-methyl-2-butyl, 1-hexyl, 1-heptyl, 1-octyl, 2-ethyl-1-hexyl, 1-nonyl, 1-decyl; or a phenyl radical which may be unsubstituted or substituted by from one to five C$_1$–C$_6$-alkyl groups, for example phenyl, 2-methylphenyl (2-tolyl), 3-methylphenyl (3-tolyl), 4-methylphenyl (4-tolyl), 2,4-dimethylphenyl, 2,6-dimethylphenyl, 2,4,6-trimethylphenyl.

Very particularly preferred carboxamides having one carboxamide group of the formula —CO—N< in the molecule are N,N-dimethylacetamide, N,N-diethylacetamide, N,N-dipropylacetamide, N,N-diisopropylacetamide, N,N-dibutylacetamide, N,N-diisobutylacetamide, N,N-dipentylacetamide, N,N-dihexylacetamide, N,N-dioctylacetamide, N,N-dimethylpropionamide, N,N-diethylpropionamide, N, N-dipropylpropionamide, N,N-diisopropylpropionamide, N,N-dibutylpropionamide, N,N-diisobutylpropionamide, N,N-dipentylpropionamide, N,N-dihexylpropionamide and N,N-dioctylpropionamide.

As carboxamides having two or more carboxamide groups of the formula —CO—N< in the molecule, it is generally possible to use monomeric, oligomeric or polymeric carboxamides in the process of the present invention.

Typical representatives of monomeric carboxamides having two or more carboxamide groups of the formula —CO—N< in the molecule are the amides of dicarboxylic and oligocarboxylic acids, for example compounds of the formula

R'$_2$N—CO—(CH$_2$)$_n$—CO—NR'$_2$, where R' is as defined above and n is from 1 to 10.

For the purposes of the present invention, oligomeric and polymeric carboxamides are carboxamides which comprise linked structural repeating units of the same type or of different types and in which at least one of these linked structural repeating units contains a carboxamide group of the formula —CO—N< and the overall oligomer or polymer contains at least two carboxamide groups of the formula —CO—N<. The dividing line between oligomeric and polymeric is not defined exactly in the relevant literature. However, the division is generally made at a molar mass of about 10,000 g/mol. The upper limit of the molar mass of the polymeric carboxamides to be used in the process of the present invention is determined by the condition of solubilizability in the reaction mixture. It is generally, depending on the type of chemical structure, from about 1000 to 200,000 g/mol.

In the process of the present invention, preference is given to using an oligomeric or polymeric carboxamide containing at least 5 carboxamide groups of the formula —CO—N< and having a molar mass in the range from 1000 to 200,000 g/mol, preferably from 5000 to 100,000 g/mol and particularly preferably from 10,000 to 100,000 g/mol. The molar mass specified is in each case a mean molar mass since the preparation of the polyamines and their further reaction usually results in a broad molar mass distribution.

The oligomeric and polymeric carboxamides are generally homooligomers, cooligomers, homopolymers and copolymers of nitrogen-containing monomer units. Suitable examples are acylated oligoalkylenimines and polyalkylenimines, in particular acylated oligoethylenimines and polyethylenimines;

acylated oligovinylamines and polyvinylamines;

oligomers and polymers of ethylenically unsaturated carboxamides, for example oligoacrylamides and polyacrylamides or oligomethacrylamides and polymethacrylamides; and oligomers and polymers of acyclic and cyclic N-vinyl amides, for example oligovinylformamides and polyvinylformamides or oligovinylcaprolactams and polyvinylcaprolactams.

The oligomers and polymers may have different nitrogen-containing monomers and, if desired, nitrogen-free monomers in one molecule. The carboxamide group of the formula —CO—N< may be present in the main chain or in side groups.

The polarity of the oligomeric or polymeric carboxamide is chosen so that it is present in solubilized form in the reaction mixture under the reaction conditions. The presence of the carboxamide groups alone achieves an appropriate polarity. It can be increased further by means of further suitable substituents. In the case of amino-containing oligomers and polymers, the polarity can be increased, for example, by means of additional substituents such as alkyl, aryl or polyoxyalkylene groups. The introduction of substituents can be carried out by reaction with suitable derivative-forming reagents, e.g. carboxylic acids, carboxylic acid derivatives, alkylating agents or alkene oxides, by phosphonomethylation, by the Strecker synthesis, etc. Derivative formation can occur at nitrogen atoms or in other positions on the oligomer or polymer. The functional groups can be introduced by polymer-analogous reaction of the nitrogen-containing oligomer or polymer or at the stage of the pair of monomers or by concomitant use of suitable copolymerizable nitrogen-free monomers.

As component (d) in the process of the present invention, particular preference is given to using an acylated oligoethylenimine or polyethylenimine comprising units of the formula (I) or branched isomers thereof

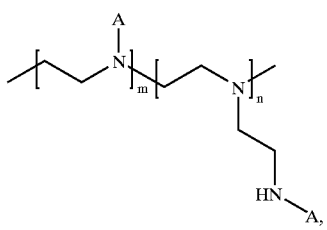

(I)

where the sum m+n is at least 10 and A are each, independently of one another, hydrogen or a —CO—R group, where R are each, independently of one another, an alkyl, cycloalkyl, aryl, aralkyl or acyl radical having up to 30 carbon atoms. The ratio m/(m+n) is preferably from 0.01 to 1.

The sum m+n is preferably at least 50 and particularly preferably at least 100. The ratio m/(m+n) is preferably from 0.3 to 1 and particularly preferably from 0.5 to 0.9.

The acylated oligoethyleneimines or polyethyleneimines (I) which are preferably used generally contain primary (—NH$_2$), secondary (>NH) and tertiary (>N—) amino groups. The ratio of primary:secondary:tertiary amino groups is generally 1:0.1–2:0.1–2 and preferably 1:0.8–1.3:0.6–1.1.

The acylated oligoethyleneimines or polyethyleneimines (I) which are preferably used comprise the following structural elements or branched isomers thereof

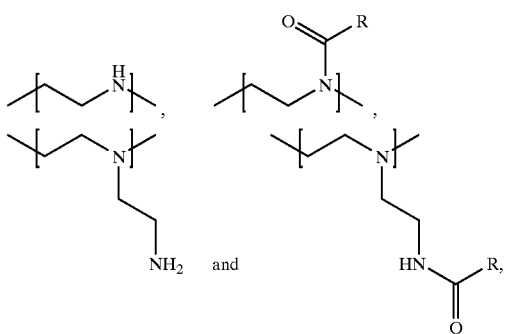

where R is as defined above.

The radical R is preferably an unbranched or branched, substituted or unsubstituted C$_1$–C$_{21}$-alkyl radical such as methyl, ethyl, 1-propyl, 2-propyl (sec-propyl), 1-butyl, 2-butyl (sec-butyl), 2-methyl-1-propyl (isobutyl), 2-methyl-2-propyl (tert-butyl), 1-pentyl, 2-pentyl, 3-pentyl, 1-hexyl, 1-heptyl, 2-heptyl, 3-heptyl, 1-octyl, 2,4,4-trimethylpentyl, 1-nonyl, 2-methyl-2-octyl, 1-decyl, 1-undecyl, 1-dodecyl, 1-tridecyl, 1-tetradecyl, 1-pentadecyl, 1-hexadecyl, 1-heptadecyl, 1-octadecyl, 1-nonadecyl, 1-eicosyl or 1-heneicosyl;

an unbranched or branched, substituted or unsubstituted cycloalkyl radical having from 5 to 20 carbon atoms, for example cyclopentyl, cyclohexyl or cyclooctyl;

a phenyl radical which may be unsubstituted or substituted by from one to five C$_1$–C$_8$-alkyl groups, for example phenyl, 2-methylphenyl (2-tolyl), 3-methylphenyl (3-tolyl), 4-methylphenyl (4-tolyl), 2,4-dimethylphenyl, 2,6-dimethylphenyl and 2,4,6-trimethylphenyl;

a substituted or unsubstituted aralkyl radical having from 7 to 20 carbon atoms, for example phenylmethyl (benzyl) or 2-phenyl-1-ethyl.

The R is particularly preferably a C$_1$–C$_6$-alkyl radical such as methyl, ethyl, 1-propyl, 2-propyl (sec-propyl), 1-butyl, 2-butyl (sec-butyl), 2-methyl-1-propyl (isobutyl), 2-methyl-2-propyl (tert-butyl), 1-pentyl, 2-pentyl, 3-pentyl or 1-hexyl.

The component (d) used in the process of the present invention is very particularly preferably an acylated oligoethylenimine or polyethylenimine (I) in which the acyl radical R—CO— corresponds to the acyl radical of the carboxylic acid which can be obtained from the α-olefin used, carbon monoxide and water in the presence of the same catalyst system. When the simplest α-olefin, viz. ethene, is used, R—CO— is thus very particularly preferably a propionyl radical CH$_3$CH$_2$—CO—.

Oligoethylenimines and polyethylenimines are generally prepared by homopolymerization or copolymerization of aziridine, if appropriate together with other monomers such as vinyl amides, vinylamines, acrylamides, acrylamines, acrylic esters, methacrylic esters and olefins such as ethene, propene, butene or butadiene, and generally have a mean molecular weight of from 200 to 200,000 g/mol.

The particularly preferred acylated oligoethylenimines and polyethylenimines (I) are generally prepared by reaction of the oligoethylenimines and polyethylenimines with carboxylic acids, for example formic acid, acetic acid, propionic acid, butyric acid, valeric acid, lauric acid, 2-ethylhexanoic acid or natural C$_{18}$-fatty acids, with the degree of amidation being from 1 to almost 100%, preferably from 30 to almost 100%, based on the amidatable amino groups. Details of the preparation may be found in DE-A 37 27 704. However, it is also possible to prepare the acylated oligoethylenimines and polyethylenimines (I) in situ under the carbonylation conditions, for example by reaction of an oligoethylenimine or polyethylenimine with an olefin and carbon monoxide in the presence of the nucleophilic compound, the palladium component and the phosphine or by reaction of the polyethylenimine with the carboxylic acid used as solvent under the conditions of the carbonylation reaction.

Furthermore, the acylated oligoethylenimine or polyethylenimine (I) may further comprise structural elements of the type

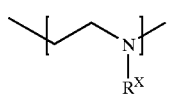

where the radical R$^x$ is defined as for the radical R or is a hydroxyalkyl(poly)oxyalkylene radical having up to 500 oxyalkylene units and preferably having from 2 to 6 carbon atoms per oxyalkylene unit. They are generally prepared by reacting the acylated oligoethylenimines and polyethylenimines with up to 500 mol of ethylene oxide, propylene oxide or butylene oxide per monomer unit of the oligoethylenimine or polyethylenimine. Details of the preparation may be found in U.S. Pat. No. 5,846,453.

The structure shown in the above formula (I) is an idealized formula for the case where the acylated oligoethylenimines and polyethylenimines shown are linear. The repeating units can be present in any order, for example a random order. The acylated oligoethylenimines and polyethylenimines to be used in the process of the present invention may also be partly branched and have, for example, structural elements of the type shown below:

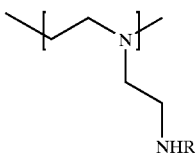

If in the present text reference is made to "branched isomers" in the context of oligoethylenimines and polyethylenimines, this refers to structural isomers derived from the structure shown by single or multiple insertion of one of the repeating units shown in brackets in formula (I) into an NH bond. They are branched via tertiary nitrogen atoms.

Further compounds suitable as component (d) in the process of the present invention are acylated oligovinylamines and polyvinylamines of the formula (III)

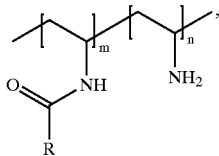
(III)

where m and n are as defined above and R are, independently of one another, as defined under (I).

Further compounds suitable as component (d) in the process of the present invention are oligoacrylamides and polyacrylamides and oligomethacrylamides and polymethacrylamides comprising, as characteristic structural element, units of the formula (IV)

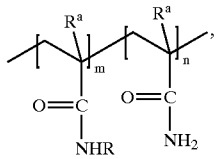
(IV)

where $R^a$ is hydrogen or methyl, R are, independently of one another, as defined under (I) and m and n are as defined above.

In general, preference is given to solubilizable nitrogen-containing polymers which are free of sulfonic acid groups.

In the process of the present invention, the carboxamide (d) is generally used in an amount of from 0.5 to 15% by weight, preferably from 1 to 10% by weight and particularly preferably from 3 to 7.5% by weight, based on the total mass of the initial reaction mixture, i.e. at the beginning of the reaction.

Possible palladium sources for component (a) in the process of the present invention are inorganic and organic salts of palladium, palladium compounds containing nitrogen-, phosphorus- and/or oxygen-containing donor ligands and also palladium or palladium compounds applied to a support. Preference is given to halogen-free palladium sources.

Examples of suitable inorganic and organic salts of palladium are palladium(II) nitrate, palladium(II) sulfate, palladium(II) carboxylates (e.g. palladium(II) acetate or palladium(II) propionate), palladium(II) sulfonates and palladium(II) acetylacetonate.

Examples of suitable palladium compounds containing nitrogen-, phosphorus- and/or oxygen-containing donor ligands are tetrakis(triphenylphosphine)palladium(0) (Pd(PPh$_3$)$_4$), dibenzylideneacetonepalladium(0) (Pd(dba)$_2$) or [Pd(dpa-3)(CH$_3$CN)$_2$] [A]$_2$, where A is a weakly coordinating anion, for example chlorate, hexafluorophosphate, tetrafluoroborate or p-toluenesulfonate, and "dpa-3" is 1,3-P,P'-di(2-phospha-1,3,5,7-tetramethyl-6,9,10-trioxatricyclo [3.3.1.1{3.7}]decyl)propane.

A suitable example of palladium applied to a support is palladium on activated carbon. Palladium sources of this type are preferably used as particles which allow suspension in the reaction mixture. The support materials are preferably hydrophilic in nature to ensure a stable suspension and may be made hydrophilic by separate measures such as surface oxidation of activated carbon.

In the process of the present invention, the palladium or the palladium compound (a) is generally used in an amount of from 0.5 to 20 mmol of palladium per liter of initial reaction mixture.

Phosphines (b) suitable for use in the process of the present invention are described, for example, in EP-A 0 274 795, EP-A 0 282 142, EP-A 0 386 833, EP-A 0 441 446, EP-A 0 495 547, EP-A 0 495 548, EP-A 0 499 329, EP-A 0 577 204, EP-A 0 577 205, WO 94/18154, WO 96/19434, WO 96/45040 and WO 98/42717, which are hereby expressly incorporated by reference. The suitable phosphines have the formula (V)

$$PR^1R^2R^3 \qquad (V)$$

where the radicals $R^1$, $R^2$ and $R^3$ are each, independently of one another, a carbon-containing organic radical. The radicals $R^1$, $R^2$ and/or $R^3$ may also be joined to one another.

For the present purposes, a carbon-containing organic radical is an unsubstituted or substituted, aliphatic, aromatic or araliphatic radical having from 1 to 30 carbon atoms. This radical can also contain one or more heteroatoms such as oxygen, nitrogen, sulfur or phosphorus, for example —O—, —S—, —NR—, —CO—, —N=, —SiR$_2$—, —PR— and/or —PR$_2$, and/or be substituted by one or more functional groups containing, for example, oxygen, nitrogen, sulfur and/or halogen atoms, for example by fluorine, chlorine, bromine, iodine and/or a cyano group (here, the radical R is likewise a carbon-containing organic radical). If the carbon-containing organic radical contains one or more heteroatoms, it can also be bound via a heteroatom. Thus, for example, ether, thioether and tertiary amino groups are also included. The carbon-containing organic radical can be a monovalent or polyvalent, for example divalent, radical.

If the phosphine (V) contains precisely one phosphorus atom, i.e. the radicals $R^1$, $R^2$ and $R^3$ contain neither a —PR— group nor a —PR$_2$— group, this will hereinafter be referred to as a monodentate phosphine. If $R^1$, $R^2$ and/or $R^3$ contain one or more —PR— or —PR$_2$— groups, the phosphines (V) are referred to as bidentate, tridentate, etc., depending on the number of phosphorus atoms.

In the process of the present invention, preference is given to using a phosphine which is at least bidentate. It can be described by the formula (VI)

(VI)

where the radicals $R^4$, $R^5$, $R^6$ and $R^7$ are each, independently of one another, a carbon-containing organic radical and X is a carbon-containing organic bridging group. The preferred phosphines (VI) are bidentate, tridentate or tetradentate, in particular bidentate.

The term carbon-containing organic radical is defined as set forth above.

For the present purposes, a carbon-containing organic bridging group is an unsubstituted or substituted, aliphatic, aromatic or araliphatic divalent group having from 1 to 20 carbon atoms and from 1 to 10 atoms in the chain. The organic bridging group may contain one or more heteroatoms such as oxygen, nitrogen, sulfur or phosphorus, for example —O—, —S—, —NR—, —CO—, —N=, —SiR$_2$—, —PR— and/or —PR$_2$, and/or be substituted by one or more functional groups containing, for example, oxygen, nitrogen, sulfur and/or halogen atoms, for example by fluorine, chlorine, bromine, iodine and/or a cyano group (here, the radical R is likewise a carbon-containing organic radical). If the organic bridging group contains one or more heteroatoms, it can also be bound via a heteroatom. Thus, for example, ether, thioether and tertiary amino groups are also included.

Monovalent radicals $R^1$, $R^2$ and $R^3$ in formula (V) and $R^4$, $R^5$, $R^6$ and $R^7$ in formula (VI) are each preferably an unbranched or branched, acyclic or cyclic, unsubstituted or substituted alkyl radical having from 1 to 20 aliphatic carbon atoms in which one or more of the CH$_2$ groups may also be replaced by heteroatoms such as —O— or —S— or by heteroatom-containing groups such as —CO—, —NR— or —SiR$_2$—, and in which one or more of the hydrogen atoms may be replaced by substituents such as aryl groups; or an unsubstituted or substituted aromatic radical which contains one ring or two or three fused rings and in which one or more ring atoms may be replaced by heteroatoms such as nitrogen and one or more of the hydrogen atoms may be replaced by substituents such as alkyl or aryl groups.

Examples of preferred monovalent radicals are unsubstituted or substituted $C_1$–$C_{20}$-alkyl, $C_5$–$C_{20}$-cycloalkyl, $C_6$–$C_{20}$-aryl and $C_3$–$C_{20}$-heteroaryl radicals, for example methyl, ethyl, 1-propyl, 2-propyl (sec-propyl), 1-butyl, 2-butyl (sec-butyl), 2-methyl-1-propyl (isobutyl), 2-methyl-2-propyl (tert-butyl), 1-pentyl, 2-pentyl, 3-pentyl, 2-methyl-2-butyl (tert-amyl), 1-hexyl, 2-hexyl, 3-hexyl, 2-methyl-2-pentyl, 3-methyl-3-pentyl, 2-methoxy-2-propyl, cyclopentyl, cyclohexyl, cyclooctyl, phenyl, 2-methylphenyl (o-tolyl), 3-methylphenyl (m-tolyl), 4-methylphenyl (p-tolyl), 2,6-dimethylphenyl, 2,4-dimethylphenyl, 2,4,6-trimethylphenyl, 2-methoxyphenyl, 3-methoxyphenyl, 4-methoxyphenyl, 2-pyridyl, 3-pyridyl, 4-pyridyl, 3-pyridazinyl, 4-pyridazinyl, 5-pyridazinyl, 2-pyrimidinyl, 4-pyrimidinyl, 5-pyrimidinyl, 2-pyrazinyl, 2-(1,3,5-triazin)yl, 1-naphthyl, 2-naphthyl, 2-quinolyl, 8-quinolyl, 1-isoquinolyl and 8-isoquinolyl.

Divalent radicals $R^1$ together with $R^2$, $R^2$ together with $R^3$ or $R^1$ together with $R^3$ in formula (V) and $R^4$ together with $R^5$ and/or $R^6$ together with $R^7$ in formula (VI) are each preferably an unbranched or branched, acyclic or cyclic, unsubstituted or substituted $C_4$–$C_{20}$-alkylene radical ("divalent alkyl radical") which has from 4 to 10 atoms in the alkylene chain and in which CH$_2$ groups may also be replaced by heterogroups, for example —CO—, —O—, —SiR$_2$— or —NR—, and in which one or more of the hydrogen atoms may be replaced by substituents such as aryl groups.

Examples of preferred divalent radicals are unsubstituted or substituted $C_4$–$C_{30}$-alkylene radicals in which CH$_2$ groups may be replaced by hetero groups such as —O—, for example 1,4-butylene, 1,4-dimethyl-1,4-butylene, 1,1,4,4-tetramethyl-1,4-butylene, 1,4-dimethoxy-1,4-butylene, 1,4-dimethyl-1,4-dimethoxy-1,4-butylene, 1,5-pentylene, 1,5-dimethyl-1,5-pentylene, 1,5-dimethoxy-1,5-pentylene, 1,1,5,5-tetramethyl-1,5-pentylene, 1,5-dimethyl-1,5-dimethoxy-1,5-pentylene, 3-oxa-1,5-pentylene, 3-oxa-1,5-dimethyl-1,5-pentylene, 3-oxa-1,5-dimethoxy-1,5-pentylene, 3-oxa-1,1,5,5-tetramethyl-1,5-pentylene, 3-oxa-1,5-dimethyl-1,5-dimethoxy-1,5-pentylene, 1,4-cyclooctylene, 1,5-cyclooctylene, 1,4-dimethyl-1,4-cyclooctylene, 1,4-dimethyl-1,5-cyclooctylene, 1,4-dimethyl-5,8-cyclooctylene, 1,5-dimethyl-1,4-cyclooctylene, 1,5-dimethyl-1,5-cyclooctylene, 1,5-dimethyl-4,8-cyclooctylen,

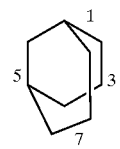

3,7-bicyclo[3.3.1]nonylene,

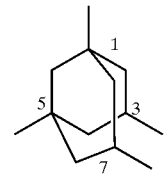

1,3,5,7-tetramethyl-3,7-bicyclo[3.3.1]nonylene,

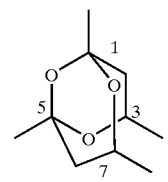

1,3,5,7-tetramethyl-4,8,9-trioxa-3,7-bicyclo[3.3.1] nonylene.

Trivalent radicals $R^1$ together with $R^2$ together with $R^3$ are each preferably an unbranched or branched, acyclic or cyclic, unsubstituted or substituted trivalent alkyl radical which has from 4 to 20 carbon atoms and in each case from 4 to 10 atoms in the chain and in which CH$_2$ groups may also be replaced by heterogroups, for example —CO—, —O— or —NR—, and in which one or more of the hydrogen atoms may be replaced by substituents such as aryl groups.

The phosphine (V) or (VI) to be used in the process of the present invention particularly preferably encompasses compounds in which the radicals $R^1$, $R^2$ and/or $R^3$ and $R^4$, $R^5$, $R^6$ and/or $R^7$ are each, independently of one another, an unsubstituted or substituted $C_3$–$C_{12}$-alkyl radical in which at least two, preferably three, further skeletal atoms are bound to the α-carbon atom or an unsubstituted or substituted aromatic radical which has six ring atoms and in which one, two or three ring atoms can also be replaced by nitrogen; and/or the radicals R¹ together with R², R² together with R³ or R¹ together with R³ and also R⁴ together with R⁵ and/or R⁶ together with R⁷ are in each case, independently of one another, an unsubstituted or substituted $C_4$–$C_{30}$-alkylene radical which has from 4 to 7 atoms in the shortest alkylene chain and in which $CH_2$ groups may be replaced by heterogroups, for example by —O—.

For the present purposes, the term skeletal atoms refers to the skeleton-forming atoms such as carbon, oxygen or nitrogen.

Examples of particularly preferred monovalent radicals R¹, R² and/or R³ and also R⁴, R⁵, R⁶ and/or R⁷ are 2-propyl (sec-propyl), 2-butyl (sec-butyl), 2-methyl-2-propyl (tert-butyl), 2-methyl-2-butyl (tert-amyl), phenyl, 2-methylphenyl (o-tolyl), 3-methylphenyl (m-tolyl), 4-methylphenyl (p-tolyl), 2,6-dimethylphenyl, 2,4-dimethylphenyl, 2,4,6-trimethylphenyl and 2-pyridyl, in particular 2-methyl-2-propyl (tert-butyl) and phenyl. Examples of particularly preferred divalent radicals R¹ together with R², R² together with R³ or R¹ together with R³ and also R⁴ together with R⁵ and/or R⁶ together with R⁷ are 1,1,4,4-tetramethyl-1,4-butylene, 1,4-dimethyl-1,4-dimethoxy-1,4-butylene, 1,1,5,5-tetramethyl-1,5-pentylene, 1,5-dimethyl-1,5-dimethoxy-1,5-pentylene, 1,5-dimethyl-1,5-cyclooctylene, 1,3,5,7-tetramethyl-3,7-bicyclo[3.3.1]nonylene and 1,3,5,7-tetramethyl-4,8,9-trioxa-3,7-bicyclo[3.3.1]nonylene, in particular 1,3,5,7-tetramethyl-4,8,9-trioxa-3,7-bicyclo[3.3.1]nonylene.

The organic bridging group X in formula (VI) is preferably an unbranched or branched, acyclic or cyclic, unsubstituted or substituted divalent aliphatic, aromatic or araliphatic group which has from 1 to 20 carbon atoms and from 1 to 8 atoms, preferably from 2 to 4 atoms, in the chain and in which one or more of the $CH_2$ groups may be replaced by heteroatoms such as —O— or by heteroatom-containing groups such as —CO— or —NR—, and/or one or more of the aromatic ring atoms may be replaced by heteroatoms such as nitrogen, and in which one or more of the hydrogen atoms may be replaced by substituents such as alkyl or aryl groups.

Examples of preferred bridging groups X are 1,2-ethylene, 1,3-propylene, 1,2-propylene, 1,4-butylene, 2-methyl-1,3-propylene, 1,5-pentylene, 2,2-dimethyl-1,3-propylene, 1,6-hexylene, —O—$CH_2CH_2$—O—, —O—$CH_2CH_2CH_2$—O—, —$CH_2$—O—$CH_2$—, —$CH_2CH_2$—O—$CH_2CH_2$—, o-phenylene, o-xylene and —$CH_2$—NR—$CH_2$—, in particular 1,2-ethylene, 1,3-propylene, 1,4-butylene and o-xylene.

A particularly preferred monodentate phosphine is triphenylphosphine. Particularly preferred bidentate phosphines are 1,2-bis(di-tert-butylphosphino)ethane, 1,2-bis(diphenylphosphino)ethane, 1,2-P,P'-di(2-phospha-1,3,5,7-tetramethyl-6,9,10-trioxatricyclo-[3.3.1.1{3.7}]decyl)ethane ("dpa-2" for short), 1,3-bis(di-tert-butylphosphino)propane, 1,3-bis(diphenylphosphino)propane, 1,3-P,P'-di(2-phospha-1,3,5,7-tetramethyl-6,9,10-trioxatricyclo-[3.3.1.1{3.7}]decyl)propane ("dpa-3" for short), 1,4-bis(di-tert-butylphosphino)butane, 1,4-bis(diphenylphosphino)butane, 1,4-P,P'-di(2-phospha-1,3,5,7-tetramethyl-6,9,10-trioxatricyclo-[3.3.1.1{3.7}]decyl)butane ("dpa-4" for short), α,α'-bis(di-tert-butylphosphino)-o-xylene, α,α'-bis(diphenylphosphino)-o-xylene and α,α-P,P'-di(2-phospha-1,3,5,7-tetramethyl-6,9,10-trioxatricyclo-[3.3.1.1{3.7}]decyl)-o-xylene, in particular 1,3-bis(di-tert-butylphosphino)propane, 1,3-bis(diphenylphosphino)propane and

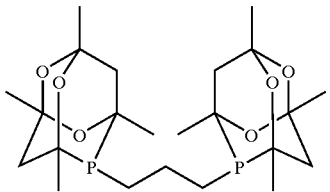

1,3-P,P'-di(2-phospha-1,3,5,7-tetramethyl-6,9,10-trioxatricyclo[3.3.1.1{3.7}]decyl)propane ("dpa-3").

In the process of the present invention, the phosphine (b) is generally used in a molar ratio to palladium of from 0.5 to 50. When using a monodentate phosphine ligand, its molar ratio to palladium is preferably in the range from 4 to 30, and when using a bidentate phosphine ligand, its molar ratio to palladium is preferably in the range from 1 to 20.

When using monodentate phosphine ligands, preference is given to using from 5 to 20 mmol, particularly preferably from 5 to 10 mmol, of palladium per liter of initial reaction mixture, and when using bidentate phosphine ligands, preference is given to using from 0.5 to 5 mmol, particularly preferably from 1 to 3 mmol, of palladium per liter of initial reaction mixture.

As component (c) in the process of the present invention, use is made of a protic acid having a $pK_a$ of $\leq 4.5$, measured in aqueous solution at 25° C.

The protic acid to be used can be an organic or inorganic protic acid. Preference is given to protic acids which form a weakly coordinating or noncoordinating anion.

Examples of suitable protic acids are
strong mineral acids such as sulfuric acid, phosphoric acid (either orthophosphoric or pyrophosphoric acid), perchloric acid and tetrafluoroboric acid;
sulfonic acids such as methanesulfonic acid, trifluoromethanesulfonic acid, chlorosulfonic acid, fluorosulfonic acid, benzenesulfonic acid, p-toluenesulfonic acid, naphthalenesulfonic acid and ion-exchange resins containing sulfonic acid groups; and
carboxylic acids such as oxalic acid, glycolic acid, chloroacetic acid, dichloroacetic acid, trichloroacetic acid and trifluoroacetic acid.

In the process of the present invention, preference is given to using protic acids (c) having a $pK_a$ of $\leq 2$, measured in aqueous solution at 25° C.

Preferred protic acids are p-toluenesulfonic acid, methanesulfonic acid, trifluoromethanesulfonic acid, trichloroacetic acid and trifluoroacetic acid.

The molar ratio of the protic acid (c) to the palladium (a) is generally not critical. It is generally in the range from 0.5 to 5000, preferably from 10 to 3000.

The catalyst system to be used in the process of the present invention can be homogeneous or heterogeneous. When using a homogeneous catalyst system, the catalyst system is solubilized in the reaction mixture and is generally homogeneously distributed. When using a heterogeneous catalyst system, the catalyst system or its precursor is generally present in particulate form. An example of this is palladium or a palladium compound deposited on a support material as component (a).

The process of the present invention is preferably carried out in a liquid phase. In this case, the catalyst system is generally solubilized substantially homogeneously in the reaction mixture. In general, the liquid carbonylation product and the protic acid used serve as solvent. However, it is also possible to carry out the reductive carbonylation in a preferred inert solvent. Solvents which are well suited for this purpose are, for example, aromatic or aliphatic hydrocarbons such as toluene, xylene or decalin and polar, aprotic solvents such as tetrahydrofuran, 1,4-dioxane, N-methylpyrrolidone, N-methylpiperidone, dimethyl sulfoxide, glycol ethers (e.g. 1,2-dimethoxyethane, bis(2-methoxyethyl) ether or bis(2-butoxyethyl) ether), dimethylformamide, dimethylformanilide, ethylene carbonate, propylene carbonate, ketones (e.g. acetone or diethyl ketone) or mixtures thereof. The process is preferably carried out in a solvent corresponding to the carbonylation product, since this introduces no further extraneous components into the system.

In the process of the present invention, the catalyst system can generally be obtained by combining the above-described components (a), (b), (c), (d) and any solvent to be used in any order. This also encompasses the use of intermediates, e.g. palladium-phosphine complexes.

For the purposes of the present invention, α-olefins are unsubstituted or substituted alkenes having at least one terminal double bond of the structure —CH═CH$_2$. Possible substituents for the part of the molecule adjacent to the terminal double bond are, for example, aryl groups, heteroaryl groups, halides or functional groups, e.g. —COOH, —COOR, —CONR$_2$, —CN or —OR. The α-olefins generally have from 2 to 30 carbon atoms. In addition to the terminal double bond, further carbon—carbon double bonds may also be present in the molecule.

The α-olefin used in the process of the present invention is preferably a C$_2$–C$_{20}$-alkene having a terminal double bond, for example ethene, propene, 1-butene, 1-pentene, 1-hexene, 1-heptene, 1-octene, 1-nonene and 1-decene. Particular preference is given to ethene, propene, 1-butene, 1-pentene and 1-hexene, in particular ethene.

The process of the present invention generally forms, except in the case of the simplest dialkyl ketone which can be prepared in the process, viz. 3-pentanone, a mixture of two isomers of the corresponding dialkyl ketone

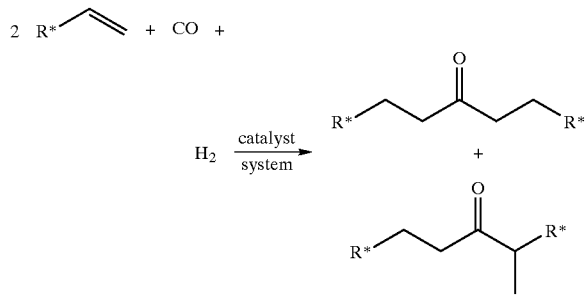

where the radical R* in the simplified reaction equation above is determined according to the above definition of the α-olefin R*—CH═CH$_2$ to be used. Thus, use of ethene results in formation of 3-pentanone (R* corresponds to hydrogen) and use of propene results in formation of a mixture of 4-heptanone and 2-methyl-3-hexanone (R* corresponds to methyl).

The preparation of 3-pentanone is particularly preferred in the process of the present invention.

The process of the present invention is generally carried out at from 40 to 200° C., preferably from 75 to 170° C., particularly preferably from 80 to 130° C. The pressure in the process of the present invention is generally from 0.1 to 20 MPa abs, preferably from 0.5 to 7 MPa abs, particularly preferably from 1 to 2.5 MPa abs.

The process of the present invention can be carried out batchwise, semicontinuously or continuously.

When the process of the present invention is carried out batchwise, the order of addition of the starting materials α-olefin, carbon monoxide and hydrogen is generally unimportant. When the process is carried out semicontinuously or continuously, the starting materials are preferably added in the stoichiometrically required ratio, i.e. α-olefin:CO:H$_2$= 2:1:1.

In a general embodiment, the catalyst system or its precursor is prepared by combining the components (a) palladium or a palladium compound, (b) phosphine, (c) protic acid having a pK$_a$ of ≦4.5, (d) solubilizable carboxamide and any solvent to be used in any order.

In a general embodiment of a batchwise process, the catalyst system or its precursor is admixed in a suitable reaction apparatus (e.g. an autoclave) with the starting materials α-olefin, carbon monoxide and hydrogen and the system is maintained under reaction conditions (pressure, temperature). After the reaction is complete, the apparatus is cooled, depressurized and the reaction product is worked up in a customary fashion, e.g. by distillation.

In a general embodiment of a semicontinuous process, the catalyst system or its precursor is admixed in a suitable reaction apparatus (e.g. an autoclave) with none, with one, two or all three, depending on the embodiment, of the starting material components and the system is brought to the reaction conditions (temperature, pressure). To set the pressure, the gaseous starting materials carbon monoxide, hydrogen and/or the α-olefin (if gaseous) are introduced. Subsequently, the necessary starting materials are introduced continuously or periodically during the course of the reaction in amounts corresponding to those in which they are consumed, preferably in the stoichiometrically required ratio. After the reaction is complete, the apparatus is cooled, depressurized and the reaction product is worked up in a customary fashion, e.g. by distillation.

In a general embodiment of a continuous process, the catalyst system or its precursor is admixed in a suitable reaction apparatus (e.g. an autoclave) with none, with one, two or all three, depending on the embodiment, starting material components and the system is brought to the reaction conditions (temperature, pressure). To set the pressure, the gaseous starting materials carbon monoxide, hydrogen and/or the α-olefin (if gaseous) are introduced. Subsequently, the three starting materials are fed in continuously in amounts corresponding to those in which they are consumed, preferably in the stoichiometrically required ratio, and a corresponding amount of the reaction mixture is continuously discharged from the reaction apparatus for work-up.

In a preferred embodiment of the continuous preparation of 3-pentanone, palladium(II) acetate, the bidentate phosphine ligand "dpa-3" (1,3-P,P'-di(2-phospha-1,3,5,7-tetramethyl-6,9,10-trioxatricyclo-[3.3.1.1{3.7}]decyl) propane), a protic acid having a pK$_a$ of ≦2 and a polyethylenimine polymer amidated with propionic acid are placed in a suitable reaction apparatus, for example a bubble column, the mixture is brought to the desired reaction temperature and to the desired reaction pressure by introduction of carbon monoxide, hydrogen and ethene. The three starting materials ethene, carbon monoxide and hydrogen are subsequently fed in continuously in the stoichiometrically required ratio. The 3-pentanone formed can then, for example, be removed continuously from the reaction apparatus by stripping it out by means of a suitable gas stream (e.g. ethene/carbon monoxide/hydrogen mixture).

The process of the present invention makes it possible to prepare dialkyl ketones in high yield from economically attractive and readily available raw materials under mild reaction conditions. The catalyst system used has a high catalytic activity and a high stability in respect of precipitation of palladium and palladium compounds. Furthermore, the process forms no undesirable coproducts. In addition, the use of the preferred oligomeric or polymeric carboxamide makes it possible for the carbonylation product to be separated from the reaction mixture in a technically simple manner, which is a decisive advantage.

EXAMPLES

The parameters referred to in this text are, unless indicated otherwise, defined as below, with DEK being the abbreviation for 3-pentanone (diethyl ketone).

Selectivity (DEK):

$$S(DEK) = DEK \text{ produced [mol]}/\{DEK \text{ produced [mol]} + \text{ethane produced [mol]} + \text{propionaldehyde produced [mol]} + \text{propionic acid produced [mol]}\}$$

Space-time yield (DEK):
STY(DEK)=DEK produced [g]/{reaction volume [1]× time [h]}
Turnover frequency:
TOF=DEK produced [mol]/{amount of palladium [mol]× time [h]}

Preparation of Component A (Amidated Polyethylenimine)

500 g of Polymin® WF (from BASF Aktiengesellschaft) were placed in a reaction vessel. Polymin® WF is a polyethylenimine having a weight average molecular weight of about 25,000 g/mol. 500 g correspond to about 11.6 mol of ethylenimine units. About 75% of the nitrogen atoms present can in principle be amidated by means of carboxylic acids, while the remaining 25% are present as tertiary amine groups.

646 g (8.72 mol) of propionic acid were added dropwise at 130° C. over a period of 2 hours under a gentle stream of nitrogen. The temperature was subsequently increased to 160° C. and the water of reaction was distilled off, with about 34 g of the propionic acid added (0.46 mol) being entrained with the water. After 4 hours, this amount of propionic acid was added again and the reaction mixture was heated at 180° C. for 15 hours. After cooling, 964 g of a polyethylenimine amidated with propionic acid, hereinafter referred to as "Polymin-PS", was obtained as a yellow-red solid.

Preparation of Component B (Diphosphine Ligand "dpa-3")

The starting material 1,3-diphosphinopropane was obtained as described by R. W. Alder et al., J. Chem. Soc., Perkin Trans. I, 1998, pages 1643 to 1655, by reaction of 1,3-dibromopropane with triethyl phosphite to form 1,3-bis(diethoxyphosphinyl)propane and subsequent reduction of the isolated intermediate with lithium aluminum hydride.

The preparation of the diphosphine ligand 1,3-P,P'-di(2-phospha-1,3,5,7-tetramethyl-6,9,10-trioxatricyclo[3.3.1.1{3.7}]decyl)-propane hereinafter referred to as "dpa-3", was carried out by a method analogous to example 1 of WO 98/42717. 4.63 mmol of 1,3-diphosphinopropane were added to a solution of 27.8 mmol of 2,4-pentanedione in 20 ml of 5M aqueous hydrochloric acid and the mixture was stirred. After about one hour, precipitation of a white solid commenced. After a further 24 hours, the volatile constituents were removed, the white product was washed with water (6 times with 20 ml each time), introduced into 20 ml of dichloromethane and dried over magnesium sulfate. After drying, the desiccant was filtered off and the solution was evaporated under reduced pressure to about 1 ml. Addition of 10 ml of anhydrous pentane resulted once again in formation of a white precipitate of "dpa-3" which was separated off and freed of residual solvent.

Experimental Procedure 1

The starting components of the catalyst system (palladium compound, phosphine, protic acid, carboxamide if used and any additional solvent used) were introduced under an argon atmosphere into a 270 ml autoclave fitted with a sparging stirrer. The autoclave was closed and a pressure of 0.4 MPa abs was set by means of a carbon monoxide/ethene/hydrogen gas mixture having a molar ratio of 1:2:1. The reaction mixture was subsequently heated to 110° C. and a pressure of 2.0 MPa abs was set by further pressurization with the carbon monoxide/ethene/hydrogen gas mixture (molar ratio=1:2:1). After one hour, the reaction mixture was cooled to room temperature, the autoclave was vented and the reaction mixture was discharged under an argon atmosphere. The composition of the liquid reaction mixture was determined by gas chromatography.

Examples 1 to 8

Examples 1 to 8 were carried out using the experimental procedure 1. Starting components used were:

EXAMPLE 1*

| Palladium compound: | 22 mg (0.1 mmol) of | palladium(II) acetate |
|---|---|---|
| Phosphine: | 95 mg (0.2 mmol) of | "dpa-3" (component B) |
| Protic acid: | 190 mg (1.0 mmol) of | p-toluenesulfonic acid |
| Carboxamide: | — | — |
| additional solvent: | 75 g of | propionic acid |

*Comparative example

EXAMPLE 2*

| Palladium compound: | 22 mg (0.1 mmol) of | palladium(II) acetate |
|---|---|---|
| Phosphine: | 95 mg (0.2 mmol) of | "dpa-3" (component B) |
| Protic acid: | 190 mg (1.0 mmol) of | p-toluenesulfonic acid |
| Carboxamide: | — | — |
| additional solvent: | 75 g of | diethylene glycol dimethyl ether |

*Comparative example

EXAMPLE 3*

| Palladium compound: | 22 mg (0.1 mmol) of | palladium(II)-acetate |
|---|---|---|
| Phosphine: | 95 mg (0.2 mmol) of | "dpa-3" (component B) |
| Protic acid: | 1.90 g (10.0 mmol) of | p-toluenesulfonic acid |
| Carboxamide: | — | — |
| additional solvent: | 75 g of | propionic acid |

*Comparative example

EXAMPLE 4

| Palladium compound: | 22 mg (0.1 mmol) | of palladium(II) acetate |
|---|---|---|
| Phosphine: | 95 mg of (0,2 mmol) | "dpa-3" (Component B) |

EXAMPLE 4-continued

| | | |
|---|---|---|
| Protic acid: | 1.90 g (10.0 mmol) | of p-toluenesulfonic acid |
| Carboxamide: | 5 g (39 mmol) of | N,N-diethylpropionamide |
| additional solvent: | 70 g of | propionic acid |

EXAMPLE 5

| | | |
|---|---|---|
| Palladium compound: | 22 mg (0.1 mmol) | of palladium(II) acetate |
| Phosphine: | 95 mg (0.2 mmol) | of "dpa-3" (component B) |
| Protic acid: | 35 g (307 mmol) | of trifluoroacetic acid |
| Carboxamide: | 28 g (217 mmol) | of N,N-diethylpropionamide |
| additional solvent: | — | — |

EXAMPLE 6

| | | |
|---|---|---|
| Palladium compound: | 22 mg (0.1 mmol) | of palladium(II) acetate |
| Phosphine: | 78 mg (0.2 mmol) | of α,α'-bis(di-tert-butyl phosphino)-o-xylene |
| Protic acid: | 35 g (307 mmol) | of trifluoroacetic acid |
| Carboxamide: | 28 g (217 mmol) | of N,N-diethylpropionamide |
| additional solvent: | — | — |

EXAMPLE 7

| | | |
|---|---|---|
| Palladium compound: | 22 mg (0.1 mmol) | of palladium(II) acetate |
| Phosphine: | 95 mg (0.2 mmol) | of "dpa-3" (component B) |
| Protic acid: | 35 g (307 mmol) | of trifluoroacetic acid |
| Carboxamide: | 28 g of | "Polymin-PS" (component A) |
| additional solvent: | — | — |

EXAMPLE 8

| | | |
|---|---|---|
| Palladium compound: | 22 mg (0.1 mmol) | of palladium(II) acetate |
| Phosphine: | 78 mg (0.2 mmol) | of α,α'-bis(di-tert-butyl phosphino)-o-xylene |
| Protic acid: | 35 g (307 mmol) | of trifluoroacetic acid |
| Carboxamide: | 28 g of | "Polymin-PS" (component A) |
| additional solvent: | — | — |

The results obtained are shown in table 1.

Comparative experiments 1 to 3 carried out in the absence of a carboxamide display a very low space-time yield STY(DEK) of max. 22 g/(l·h), a very low turnover frequency TOF of max. 224 mol/(mol·h) and an unsatisfactorily low selectivity of max. 80.2%.

In the presence of a low molecular weight carboxamide, for example N,N-diethylpropionamide in examples 4, 5 and 6, a significantly higher space-time yield STY(DEK) of up to 404 g/(l·h), a distinctly higher turnover frequency TOF of up to 2542 mol/(mol·h) and a high selectivity of up to 99.2% are achieved.

In the presence of the particularly preferred polymeric carboxamide, for example "Polymin-PS" in examples 7 and 8, a space-time yield STY(DEK) of up to 800 g/(l·h), a turnover frequency TOF of up to 5033 mol/(mol·h) and a selectivity of up to 99.6% are achieved. Furthermore, comparison of example 7 with example 8 shows that "dpa-3" as ligand leads to a better performance (STY(DEK), TOF and selectivity) than does α,α'-bis(di-tert-butylphosphino)-o-xylene).

In comparative examples 1 to 3 carried out in the absence of a carboxamide, precipitation of metallic palladium was observed. In examples 4 to 8 according to the present invention, no precipitation of metallic palladium was found in the presence of a carboxamide.

TABLE 1

Overview of the results

| Ex. | STY (DEK) [g/(1·h)] | TOF [mol/(mol·h)] | S (DEK) [%] | Pd precipitation |
|---|---|---|---|---|
| 1* | 2 | 22 | 80.2 | yes |
| 2* | 22 | 224 | 54.2 | yes |
| 3* | 10 | 110 | 81.3 | yes |
| 4 | 63 | 543 | 98.8 | none |
| 5 | 404 | 2542 | 99.2 | none |
| 6 | 350 | 2202 | 98.4 | none |
| 7 | 800 | 5033 | 99.6 | none |
| 8 | 750 | 4718 | 99.2 | none |

*Comparative experiment

We claim:

1. A process for preparing dialkyl ketones by reductive carbonylation of α-olefins by means of carbon monoxide and hydrogen in the presence of a catalyst system comprising
    (a) palladium or a palladium compound;
    (b) a phosphine;
    (c) a protic acid having a $pK_a$ of $\leq 4.5$, measured in aqueous solution at 25° C.; and
    (d) a solubilizable carboxamide.
2. The process of claim 1, wherein the carboxamide (d) is an oligomeric or polymeric carboxamide containing at least 5 carboxamide groups of the formula —CO—N< and having a molar mass in the range from 1000 to 200,000 g/mol.
3. The process of claim 2, wherein the oligomeric or polymeric carboxamide is an acylated oligoethylenimine or polyethylenimine comprising units of the formula (I) or branched isomers there

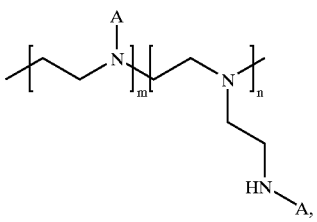

(I)

where the sum m+n is at least 10 and A are each, independently of one another, hydrogen or a —CO—R group, where R are each, independently of one another, an alkyl, cycloalkyl, aryl, aralkyl or acyl radical having up to 30 carbon atoms.

4. The process of claimed in claim 1, wherein the carboxamide (d) is used in an amount of from 0.5 to 15% by weight, based on the total mass of the initial reaction mixtures.
5. The process of claim 1, wherein the palladium or the palladium compound (a) is used in an amount of from 0.5 to 20 mmol of palladium per liter of initial reaction mixture.
6. The process of claim 1, wherein the phosphine (b) is an at least bidentate phosphine.
7. The process of claim 1, wherein the phosphine (b) is used in a molar ratio to palladium of from 0.5 to 50.
8. The process of claim 1, wherein the protic acid (c) is a protic acid having a $PK_a$ of $\leq 2$, measured in aqueous solution at 25° C.
9. The process of claim 1, wherein the reductive carbonylation is carried out at from 40 to 200° C. and a pressure of from 0.1 to 20 MPa abs.
10. The process of claim 1, in which 3-pentanone is prepared.

* * * * *

UNITED STATES PATENT AND TRADEMARK OFFICE
CERTIFICATE OF CORRECTION

PATENT NO. : 6,723,882 B2
DATED : April 20, 2004
INVENTOR(S) : Slany et al.

It is certified that error appears in the above-identified patent and that said Letters Patent is hereby corrected as shown below:

Column 18,
Line 33, "...branched isomers there..." should read -- ...branched isomers thereof... --
Line 49, "The process of..." should read -- The process as... --

Signed and Sealed this

Twenty-second Day of March, 2005

JON W. DUDAS
*Director of the United States Patent and Trademark Office*